US012620497B2

(12) United States Patent
Nguyen et al.

(10) Patent No.: US 12,620,497 B2
(45) Date of Patent: May 5, 2026

(54) DISEASE FEATURE RECOGNITION IN DIAGNOSTIC IMAGES AND DISEASE PROGRESSION PREDICTION

(71) Applicant: KONINKLIJKE PHILIPS N.V., Eindhoven (NL)

(72) Inventors: Man M Nguyen, Melrose, MA (US); Jochen Kruecker, Andover, MA (US); Raghavendra Srinivasa Naidu, Auburndale, MA (US); Haibo Wang, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 312 days.

(21) Appl. No.: 18/265,485

(22) PCT Filed: Dec. 7, 2021

(86) PCT No.: PCT/EP2021/084493
§ 371 (c)(1),
(2) Date: Jun. 6, 2023

(87) PCT Pub. No.: WO2022/122692
PCT Pub. Date: Jun. 16, 2022

(65) Prior Publication Data
US 2024/0029896 A1 Jan. 25, 2024

Related U.S. Application Data

(60) Provisional application No. 63/122,558, filed on Dec. 8, 2020.

(51) Int. Cl.
| | |
|---|---|
| G16H 50/20 | (2018.01) |
| G06T 7/00 | (2017.01) |
| G16H 50/50 | (2018.01) |

(52) U.S. Cl.
CPC ........... G16H 50/50 (2018.01); G06T 7/0012 (2013.01); G16H 50/20 (2018.01);
(Continued)

(58) Field of Classification Search
CPC ...... G16H 50/50; G16H 50/20; G06T 7/0012; G06T 2200/24; G06T 2207/10081;
(Continued)

(56) References Cited

U.S. PATENT DOCUMENTS

| | | | |
|---|---|---|---|
| 6,443,896 | B1 | 9/2002 | Detmer |
| 6,530,885 | B1 | 3/2003 | Entrekin et al. |
| (Continued) | | | |

FOREIGN PATENT DOCUMENTS

| | | |
|---|---|---|
| KR | 20180040287 A | 4/2018 |
| WO | 2018222755 A1 | 12/2018 |
| WO | 2019083227 A1 | 5/2019 |

OTHER PUBLICATIONS

Wen et al. (CN 111653365 A, machine translate document, Published Sep. 11, 2020) (Year: 2020) (Year: 2020).*
(Continued)

*Primary Examiner* — Juan M Guillermety

(57) ABSTRACT

The present disclosure describes systems configured to recognize indicators of a medical condition within a diagnostic image and predict the progression of the medical condition based on the recognized indicators. The systems can include neural networks trained to extract disease features from diagnostic images and neural networks configured to model the progression of such features at future time points selectable by a user. Modeling the progression may involve factoring in various treatment options and patient-specific information. The predicted outcomes can be displayed on a user interface customized to specific representations of the predicted outcomes generated by one or more
(Continued)

of the underlying neural networks. Representations of the predicted outcomes include synthesized future images, probabilities of clinical outcomes, and/or descriptors of disease features that may be likely to develop over time.

14 Claims, 7 Drawing Sheets

(52) U.S. Cl.
CPC ..................... *G06T 2200/24* (2013.01); *G06T 2207/10081* (2013.01); *G06T 2207/10088* (2013.01); *G06T 2207/10132* (2013.01); *G06T 2207/20076* (2013.01); *G06T 2207/20081* (2013.01); *G06T 2207/20084* (2013.01); *G06T 2207/20092* (2013.01); *G06T 2207/30096* (2013.01); *G06T 2207/30101* (2013.01)

(58) Field of Classification Search
CPC . G06T 2207/10088; G06T 2207/10132; G06T 2207/20076; G06T 2207/20081; G06T 2207/20084; G06T 2207/20092; G06T 2207/30096; G06T 2207/30101
See application file for complete search history.

(56) References Cited

U.S. PATENT DOCUMENTS

| | | | | |
|---|---|---|---|---|
| 11,756,667 | B2 * | 9/2023 | Lou ........................ | G06T 7/0012 600/408 |
| 2002/0070970 | A1 | 6/2002 | Wood et al. | |
| 2004/0101176 | A1 | 5/2004 | Mendonca et al. | |
| 2019/0027249 | A1 * | 1/2019 | Fuksenko .............. | G16H 50/30 |
| 2020/0160999 | A1 * | 5/2020 | Rim ....................... | G06T 7/0012 |
| 2020/0286229 | A1 * | 9/2020 | Ogino .................... | A61B 5/055 |
| 2020/0364864 | A1 * | 11/2020 | Shanbhag ............. | G06T 7/0012 |
| 2021/0169349 | A1 * | 6/2021 | Madabhushi ......... | G06T 7/0012 |
| 2022/0138949 | A1 * | 5/2022 | Enzmann .............. | G06T 7/0012 382/128 |

OTHER PUBLICATIONS

International Search Report and Written Opinion for PCT/EP2021/084493; Mailing date: Apr. 8, 2022, 8 pages.
Albright, J., "Forecasting the Progression of Alzheimer's Disease Using Neural Networks and a Novel Pre-Processing Algorithm", arXiv:1903.07510v2, 2019, 10 pages.
Rathore, S. et al., "A review on neuroimaging-based classification studies and associated feature extraction methods for Alzheimer's disease and its prodromal stages", NeuroImage, 2017, vol. 155, pp. 530-548.
Lundervold, A.S. et al., "An overview of deep learning in medical imaging focusing on MRI", arXiv:1811.10052v2, 2018, 44 pages.
Anonymous, "Early Detection Facts and Figures", Canary Foundation, 2009, 2 pages.
Bruno, M.A. et al., "Understanding and Confronting Our Mistakes: The Epidemiology of Error in Radiology and Strategies for Error Reduction", RadioGraphics, 2015, vol. 35, No. 6, pp. 1668-1676.
Wang, Z. et al., "Face aging with identity-preserved conditional generative adversarial networks", 2018 IEEE/CVF Conference on Computer Vision and Pattern Recognition, 2018, pp. 7939-7947.
Duong, C. et al., "Temporal non-volume preserving approach to facial age-progression and age-invariant face recognition", IEEE International Conference on Computer Vision, 2017, pp. 3755-3763.
Zhang, Z. et al., "Age Progression/Regression by Conditional Adversarial Autoencoder", arXiv:1702.08423, 2017, 9 pages.
Wang, W. et al., "Recurrent Face Aging", IEEE Conference on Computer Vision and Pattern Recognition, 2016, pp. 2379-2386.
Duong, C. et al., "Longitudinal face modeling via temporal deep restricted Boltzmann machines", IEEE Conference on Computer Vision and Pattern Recognition, 2016, 5772-5780.

* cited by examiner

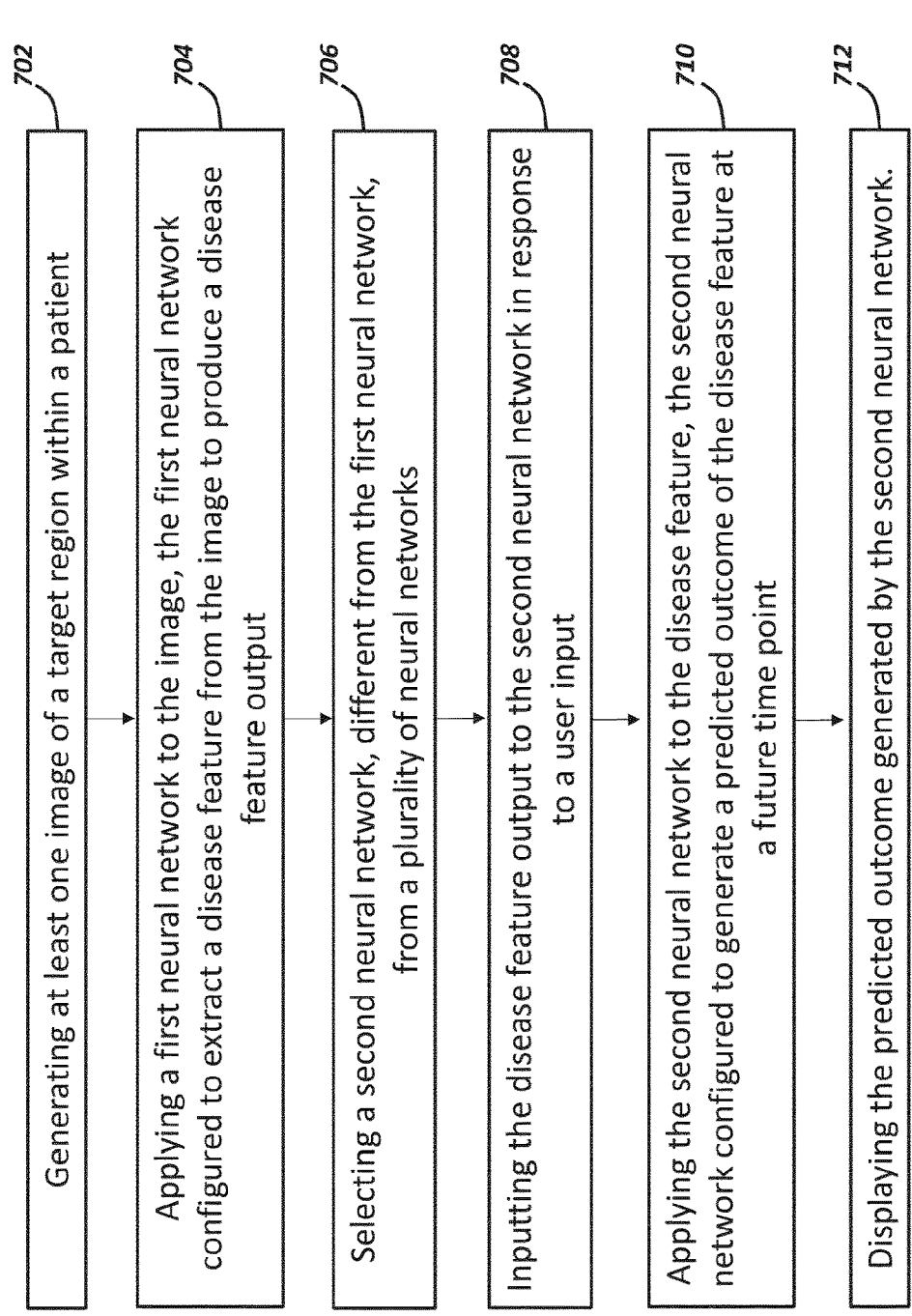

702 Generating at least one image of a target region within a patient

704 Applying a first neural network to the image, the first neural network configured to extract a disease feature from the image to produce a disease feature output 706 Selecting a second neural network, different from the first neural network, from a plurality of neural networks 708 Inputting the disease feature output to the second neural network in response to a user input 710 Applying the second neural network to the disease feature, the second neural network configured to generate a predicted outcome of the disease feature at a future time point 712 Displaying the predicted outcome generated by the second neural network.

DISEASE FEATURE RECOGNITION IN DIAGNOSTIC IMAGES AND DISEASE PROGRESSION PREDICTION

CROSS-REFERENCE TO PRIOR APPLICATIONS

This application is the U.S. National Phase application under 35 U.S.C. § 371 of International Application No. PCT/EP2021/084493, filed on Dec. 7, 2021, which claims the benefit of U.S. Provisional Patent Application No. 63/122,558, filed on Dec. 8, 2020. These applications are hereby incorporated by reference herein.

TECHNICAL FIELD

The present disclosure pertains to systems and methods for diagnosing and predicting the progression of various medical conditions. Particular implementations include systems configured to identify a disease feature in a patient image and predict the future progression of the feature with or without treatment using at least one neural network communicatively coupled with a graphical user interface.

BACKGROUND

Early detection and diagnosis is a critical first step for determining and quickly administering the best mode of treatment for a variety of medical conditions. For example, the likelihood of survival for a cancer patient is much greater if the disease is diagnosed when still confined to its original organ. Survival rates decline significantly thereafter, as tumors quickly grow and metastasize.

Despite significant advancements in medical imaging modalities, clinically-relevant features imperative for early diagnosis are often missed or underestimated by clinicians during patient examination, even when such features are captured in at least one diagnostic image. This type of error, estimated to occur at a rate of 42%, significantly impedes the accuracy and reliability of diagnostic radiology. Unnoticed features not clearly present at the time of the first image acquisition typically develop and become more noticeable during follow-up imaging sessions, but at that point the prognosis may be much worse. Improved technologies are therefore needed to identify imaged disease features earlier and more accurately than preexisting systems.

SUMMARY

The present disclosure describes systems and methods for more quickly and accurately diagnosing a patient with a medical condition and predicting the future progression of the condition in response to various treatments. Systems disclosed herein can include or be communicatively coupled with at least one image acquisition system configured to image a patient. Systems can also include at least one graphical user interface configured to display an image generated by the image acquisition system. The graphical user interface can also activate and display the output of one or more neural networks configured to receive and process the image in a manner specified via user input. Input received or obtained at the graphical user interface can include patient-specific characteristics and selectable treatment options. Output displayed on the user interface can include a synthesized image of a disease feature at a user-specified future time point, a probability of one or more clinical outcomes, and/or signs of disease progression.

Training of the neural networks utilized to generate these outputs may be tailored to the objectives of the user and the information specific to the patient.

In accordance with some examples, a disease prediction system, which may be ultrasound-based, may include an image acquisition device configured to generate at least one image of a target region within a patient. The system can also include one or more processors in communication with the image acquisition device. The one or more processors can be configured to apply a first neural network to the image, the first neural network configured to extract a disease feature from the image to produce a disease feature output. The processors can also be configured to input the disease feature output to a second neural network, different from the first neural network, in response to a user input. The processors can also be configured to apply the second neural network to the disease feature, the second neural network configured to generate a predicted outcome of the disease feature at a future time point. The system can also include a graphical user interface configured to receive the user input and display the predicted outcome generated by the second neural network.

In some examples, the second neural network is selected from a plurality of neural networks. In some embodiments, each of the plurality of neural networks is configured to generate a unique representation of the predicted outcome. In some examples, the unique representation of the predicted outcome comprises a synthesized image of the diseased feature, a probability of at least one clinical outcome, or a list of disease descriptors. In some embodiments, the user input comprises a selection of the synthesized image of the diseased feature, the probability of a clinical outcome, or the list of future disease features. In some examples, the user input comprises a treatment option, patient-specific information, or both. In some embodiments, the disease feature comprises a tumor, a lesion, an abnormal vascularization, or a combination thereof. In some examples, the image acquisition system comprises an ultrasound system, an MRI system, or a CT system. In some embodiments, the future time point is selectable by a user and is between one week and one year from a current date. In some examples, the first neural network is operatively associated with a training algorithm configured to receive an array of training inputs and known outputs, where the training inputs comprise a longitudinal sample of images obtained from patients having a medical condition, and the known outputs comprise images of the disease feature. In some embodiments, the second neural network is operatively associated with a training algorithm configured to receive a second array of training inputs and known outputs, where the training inputs comprise the disease feature and the known outputs comprise the predicted outcome.

In accordance with some examples, a method of disease prediction may involve generating at least one image of a target region within a patient and applying a first neural network to the image, the first neural network configured to extract a disease feature from the image to produce a disease feature output. The method may further involve inputting the disease feature output to a second neural network, different from the first neural network, in response to a user input. The method may also involve applying the second neural network to the disease feature, the second neural network configured to generate a predicted outcome of the disease feature at a future time point. The method may also involve displaying the predicted outcome generated by the second neural network.

In some examples, the method may further involve selecting the second neural network from a plurality of neural networks. In some embodiments, each of the plurality of neural networks is configured to generate a unique representation of the predicted outcome. In some examples, the unique representation of the predicted outcome comprises a synthesized image of the diseased feature, a probability of a clinical outcome, or a list of disease descriptors. In some embodiments, the user input comprises a selection of the synthesized image of the diseased feature, the probability of a clinical outcome, or the list of disease descriptors. In some examples, the user input comprises a treatment option, patient-specific information, or both. In some embodiments, the disease feature comprises a tumor, a lesion, an abnormal vascularization, or a combination thereof. In some examples, generating at least one image of a target region within a patient comprises acquiring ultrasound echoes generated in response to ultrasound pulses transmitted at the target region.

Any of the methods described herein, or steps thereof, may be embodied in a non-transitory computer-readable medium comprising executable instructions, which when executed may cause one or more hardware processors to perform the method or steps embodied herein.

BRIEF DESCRIPTION OF THE DRAWINGS

FIG. 7 is a flow diagram of a method of performed in accordance with embodiments of the present disclosure.

DETAILED DESCRIPTION

Figure 1:
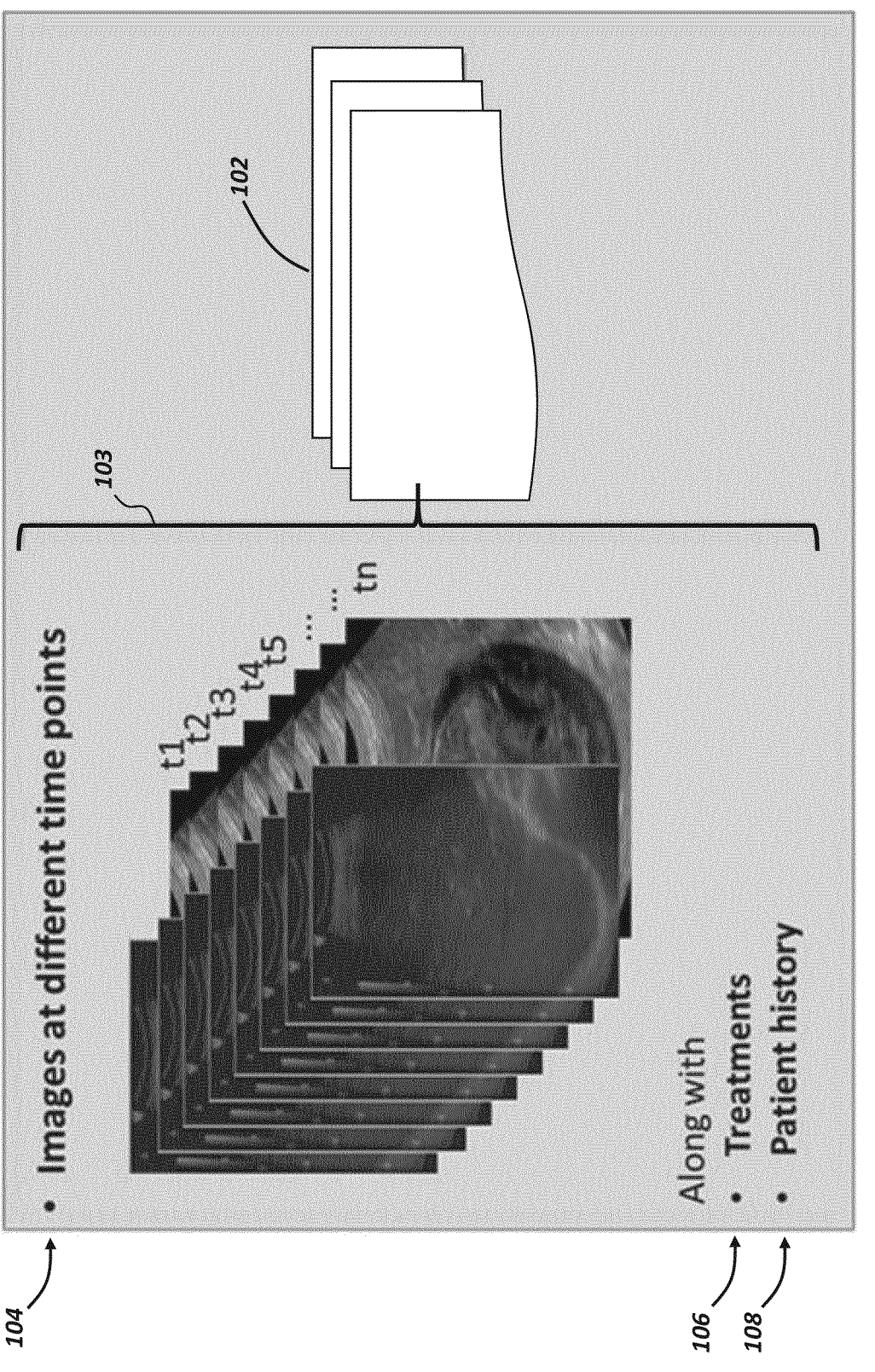
FIG. 1 is a schematic of a neural network training phase implemented in accordance with embodiments of the present disclosure.

The following description of certain embodiments is merely exemplary in nature and is in no way intended to limit the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

As used herein, the term "disease feature" may include an abnormal characteristic or attribute, a lesion, a tumor, a region of inflammation, or other indicators of a medical condition present within a patient image.

A non-limiting list of diseases or medical conditions addressed according to embodiments described herein can include liver disease, vascular disease, and/or various forms of cancer, e.g., ovarian, breast, pancreatic, lung, prostate, and/or brain cancer, just to name a few.

The technology disclosed herein can be used to prevent, minimize or reduce the frequency of missed or underestimated diagnoses by recognizing disease features that, while captured in at least one diagnostic image, may be poorly developed and thus difficult to notice. The technology may also reduce the number of unnecessary or poorly-timed patient follow-up visits to a hospital. For instance, embodiments may be configured to determine that an abnormal lesion will likely develop into a diagnosable tumor within a one-month period, which may prompt a clinician to schedule a follow-up appointment in one month as opposed to three months, for example. The disclosed technology can also reduce the likelihood and frequency at which clinicians implement sub-optimal treatment programs by predicting the likely disease progression in response to various treatment options.

To accomplish these objectives, systems disclosed herein may include a feature extraction neural network configured to receive an acquired image, e.g., an ultrasound image, and recognize one or more features indicative of a medical condition therein, such as a tumor. The acquired image can be displayed on a graphical user interface, which can receive user input and in response to the input, direct the system to process the image using one or more additional neural networks. Such networks may be referred to as policy networks herein, and they may be configured to receive output from the extraction network and generate the probability of certain changes occurring in the identified disease feature(s) at future time points in response to various treatments. Accordingly, the graphical user interface can be configured both to display output received from the policy network(s) and to receive instructions for policy network selection. The systems disclosed herein may also be patient-specific, such that the predictions of disease progression may be based at least in part on a patient's physical condition, medical history, and other factors.

FIG. 1 is a schematic of a neural network training phase implemented in accordance with various embodiments. The particular neural network(s) implemented in embodiments described herein may vary, depending for example on input received from the user. Embodiments can employ one or more neural networks to perform feature extraction, and one or more different neural networks to predict disease progression. As shown, one or more neural networks 102, e.g., feature extraction networks and policy networks, can be configured to receive a variety of training inputs 103. Such inputs 103 can include longitudinal samples of images 104 indicative of medical conditions obtained at multiple time points $(t_1, t_2, t_3, t_4 \ldots t_n)$, treatment approaches 106 implemented to address the disease features present within the images 104, and patient histories 108 specific to the patients from which the images were obtained. By training the networks 102 to learn how various disease features captured within the images 104 progressed over time in view of the treatments applied and the patient histories, the networks 102 can learn to predict the manner in which a current image containing a disease feature may progress over time in response to various treatments.

To improve the accuracy and sensitivity of the neural networks 102, the largest number of images 104 collected at the greatest possible frequency should be utilized. The training images 104 can be collected retrospectively from past studies, or prospectively through one or more forthcoming studies. In some examples, the images 104 can be obtained from a clinical database that stores a diverse variety of anatomical images. The implemented treatments 106 can include various medications, therapies, surgical operations, diets, etc. The patient histories 108 can include one or more patient characteristics, which can include age, ethnicity, body mass index (BMI), preexisting conditions, body weight, family medical histories, etc.

In some embodiments, one or more of the neural networks 102 can be configured to perform the methods described herein may be trained via one-shot synthesis and/or multiple-shot synthesis, both of which may require longitudinal samples of images 104. Through this form of training, the neural networks 102 can learn to identify trends and patterns within the individuals represented in the training population, even if a given disease feature has not been presented to the networks previously.

The neural networks 102 may be hardware- (e.g., neurons are represented by physical components) or software-based (e.g., neurons and pathways implemented in a software application), and can use a variety of topologies and learning algorithms for training the neural network to produce the desired output. For example, a software-based neural network may be implemented using a processor (e.g., single or multi-core CPU, a single GPU or GPU cluster, or multiple processors arranged for parallel-processing) configured to execute instructions, which may be stored in a computer-readable medium, and which when executed cause the processor to perform a machine-trained algorithm for identifying various indicators of disease within images of a patient and, in some examples, output an indication of the presence or absence of such indicators, thereby reducing the likelihood that such features are missed by a clinician analyzing the images. The neural networks 102 may be implemented, at least in part, in a computer-readable medium comprising executable instructions, which when executed by a processor, may cause the processor to perform a machine-trained algorithm to identify disease features present within a current image and predict the progression of such features over time. In various examples, the neural network(s) may be trained using any of a variety of currently known or later developed machine learning techniques to obtain a neural network (e.g., a machine-trained algorithm or hardware-based system of nodes) that is configured to analyze input data in the form of image frames and identify certain features, including the presence and in some embodiments, the size, of one or more disease features. Neural networks implemented herein may also be configured to analyze data output from a first neural network, to model the progression of that output. For example, an image of a tumor identified by a first neural network may be input into a second neural network configured to model the potential progression of the tumor over time.

A neural network training algorithm associated with one or more of the neural networks 102 can be presented with thousands or even millions of training data sets in order to train the neural network to identify disease features and predict the future progression of such features. In various examples, the number of images used to train each neural network may range from about to 200,000 or more. The number of images used to train a network may be increased if higher numbers of medical conditions are to be assessed. The number of training images may differ for different anatomical features, as well, and may depend on variability in the appearance of certain features. For example, images of various organs obtained from patients of various ages can be evaluated according to the systems disclosed herein. In some embodiments, the training may be supervised. For instance, the final output of a policy network, which may include a synthesized image or clinical outcome classification, may be either confirmed or rejected by an expert.

Figure 2:
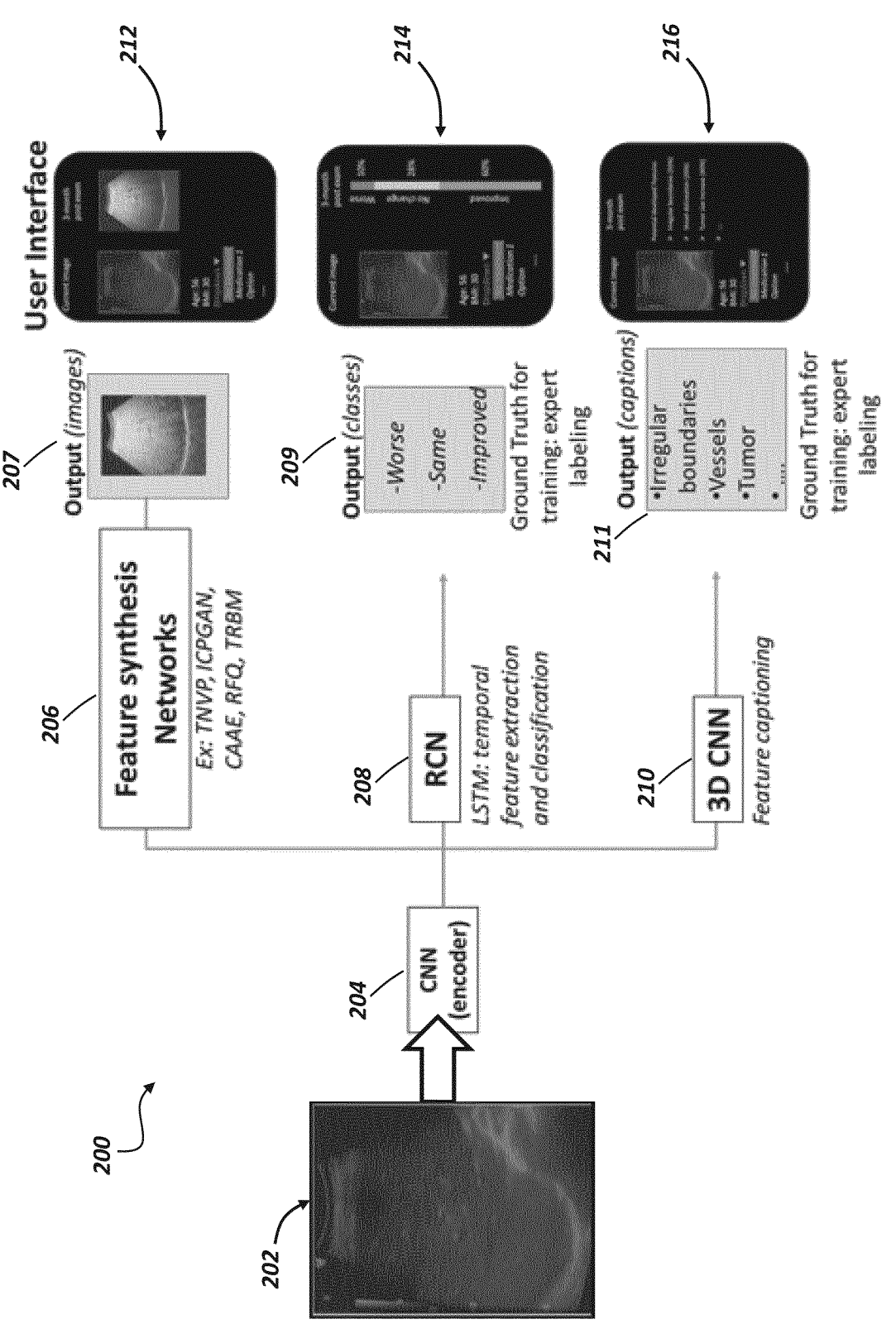
FIG. 2 is a schematic of various neural networks and graphical user interface displays generated in accordance with embodiments of the present disclosure.

FIG. 2 shows an overview of a system 200 implemented according to one or more embodiments. The system 200 includes various neural networks that may be trained and implemented according to examples described herein, along with the graphical user interface displays that may be linked to one or more of the neural networks. As shown, a current image 202, e.g., an image obtained in real-time or a recently obtained image, can be input to an extraction network 204, which is a convolutional neural network (CNN) in the example shown, configured to identify or extract a possible disease feature, if present in the image 202. The extraction network 204 may be considered the initial or first neural network due to its position within the order of operations depicted in FIG. 2. The extraction network 204 can be configured to extract one or more disease features present within the image 202 by recognizing the features as being similar to disease features contained within one or more images used to train the network 204. Accordingly, the extraction network 204, or "first network," can be trained by receiving an array of training inputs comprising a longitudinal sample of images from patients having a medical condition. The extraction network 204 can be further trained with an array of known outputs, each corresponding to a specific input, and comprising images of the disease feature identified and confirmed, e.g., via expert analysis, within the input images and associated with the medical condition. The output from the first neural network 204 can then be input to at least one of three different policy neural networks: a feature synthesis network 206, a temporal feature extraction and classification network 208, and/or a feature captioning network 210. The policy networks, each of which may be considered a parallel "second network" in this particular embodiment, can be trained by receiving an array of identified disease features, such as those extracted and output from the extraction network 204. The policy networks can be further trained with an array of known outputs comprising predicted outcomes associated with the disease feature(s). For example, known outputs used to train the feature synthesis network 206 can include images derived from patients having the identified disease feature at various time points. Outputs used to train the temporal feature extraction and classification network 208 can include categorical outcomes indicative of disease progression, for example indicating that the disease feature is worse, the same, or improved. Outputs used to train the feature captioning network 210 can include qualitative descriptors of the disease feature, for example relating to the feature's size or vascularization.

The feature synthesis network 206 can be configured to synthesize a projected future image 207 embodying the predicted progression of the disease feature detected by the extraction network 204. Examples of the feature synthesis network 206 can include a temporal non-volume preserving transformation (TNVP), an identity-preserved conditional GAN (ICPGAN), a conditional adversarial autoencoder (CAAE), a recurrent face-aging network (RFQ), or a Temporal and Spatial Restriction Boltzmann Machine (TRBM), each of which may be trained in an organ- and disease-specific manner. Variations of one or more of these networks can also be utilized. A TNVP network may operate by decomposing a disease progression into multiple sub-periods, and learning to capture disease progression features between successive sub-periods. Based on this information this form of policy network may then synthesize a final image of disease progression at one or more future time points.

The temporal feature extraction and classification network 208 can be configured to generate one or more clinical outcome probabilities 209 based on the predicted progression of the disease feature detected by the extraction network 204. As shown, the clinical outcomes may be depicted as general classes including but not limited to a "worse" outcome, a "no change" outcome, and an "improved" outcome. The ground truth used for training the temporal feature extraction and classification network 208 can include expert labeling of images obtained from patients at various stages of disease progression. In the particular example shown, the temporal feature extraction and classification network comprises an RCN.

The feature captioning network 210 can be configured to generate one or more pre-defined, disease-related feature descriptors 211 that may develop over time, e.g., irregular boundaries, vessels, tumors, etc. The ground truth used for training the feature captioning network 210 can include expert labeling of anatomical features within images obtained from patients at various stages of disease progression. Such labeling can include various descriptors indicative of a disease or its progression. For example, categorical feature descriptors such as "boundary irregularity" and "vessel delineation" can be paired with a numerical severity level, e.g., on a scale of 1-5, or a percentage indicative of a relative change in the size or extent of the feature descriptors. The associated policy network can be trained to receive the current image at time t, along with the patient-specific factors, and predict the qualitative labels and probabilities at time t+x. In the particular example shown, the feature captioning network comprises a 3D CNN.

As further shown, each output generated specifically by one policy neural network can be displayed on a uniquely configured user interface. For example, the synthesized image output 207 generated by the feature synthesis network 206 may be displayed on a first user interface 212 configured to display synthesized images. The clinical outcome probabilities 209 generated by the temporal feature extraction and classification network 208 can be displayed on a second user interface 214 configured to display the probabilities. The disease-related feature descriptors 211 generated by the feature captioning network 210 can be displayed on the third user interface 216. A user may select a desired prediction output at a user interface, which as shown in FIG. 2, may correspond to one or more specific neural networks. In this manner, the user interface may be configured to both activate the neural network processing of the system 200 and display the final output.

Figure 3:
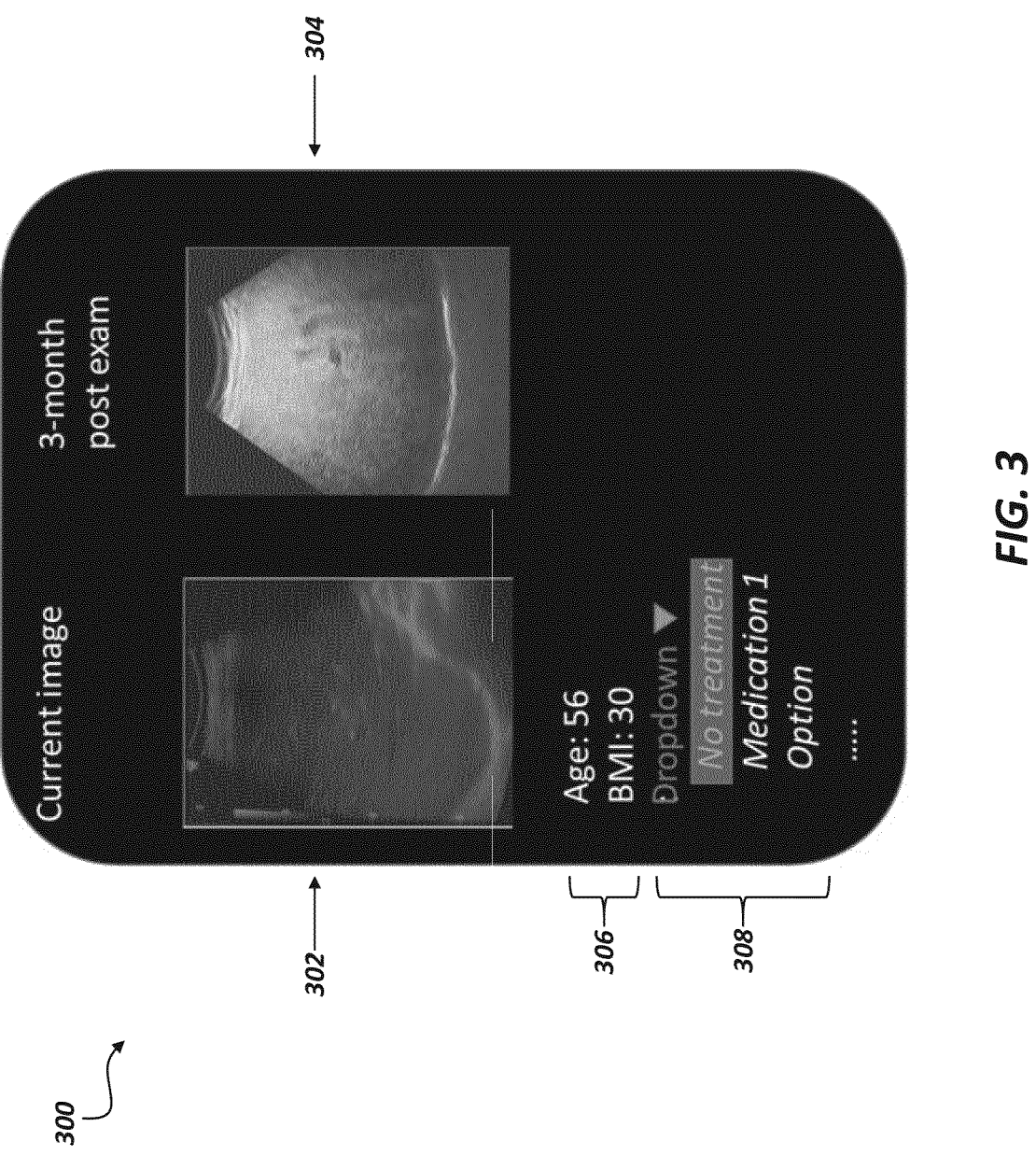
FIG. 3 is a graphical user interface configured to generate and display a predicted future image of a disease feature based on a current image in accordance with embodiments of the present disclosure.

FIG. 3 shows a graphical user interface (GUI) 300 configured to display a synthesized future image of one or more disease features detected in a current image. As shown, the GUI 300 can be configured to display a current image 302 and a synthesized future image 304 side-by-side. In this example, the synthesized future image 304 is an image projected to be obtained three months after the current image. The GUI 300 can also display patient-specific information 306 and a plurality of selectable treatment options 308, which are arranged in a dropdown menu.

In operation, a user may view the current image 302, for example during a diagnostic imaging procedure. The user may then instruct the system, for example via the user interface, to generate a synthesized future image 304. Before doing so, the user may also input one or more patient-specific factors 306 and select one or more of the treatment options 308, each of which may impact the appearance of the synthesized future image 304. The system thus enables users to determine which treatment option is appropriate or best for combating a potential disease feature captured in a current image derived from a specific patient based on that patient's medical history, physical characteristics, etc.

In some examples, the GUI 300 may be configured to prompt the user for specific patient information in response to a user input instructing the system to generate a synthesized future image. Relevant patient-specific factors may vary. For example, patient-specific information may include one or more measurements obtained the day of the current imaging session. Such factors may include a patient's weight, height, BMI, blood pressure, heart rate, etc. Patient-specific factors can also include information such as a genotype or phenotype of the patient. The patient-specific factors can be stored in a database communicatively coupled to the GUI 300 or may be entered manually during or before an exam. In some examples, a database of electronic medical records may be communicatively coupled with the system.

The GUI 300 can also provide selectable time points used to generate the synthesized future image 304. The time points may vary, and may be selectable in defined increments, e.g., daily, weekly, monthly and/or yearly time points, as measured from the current time. Specific embodiments of the GUI 300 can be configured to display a menu of discrete time points from which the user may choose. In addition or alternatively, the time point can be any time point entered by a user. In the example shown, the synthesized future image 304 provides an estimate of disease progression at three months post-exam.

Upon receiving the patient information, treatment selection and future time point, the current image 302 may be transformed into the synthesized future image 304 by embedding components of disease progression features into the current image 302. The synthesized features are then mapped back to the input image.

The process of generating the synthesized future image 304 may be repeated one or more times. For example, the user may choose to generate a new future image by selecting a different treatment approach, thereby enabling the user to assess the likely outcomes of multiple treatment options. The user may also select a different time point to get a better idea of how quickly the medical condition could progress. Presented with GUI 300, a user may be supplied with information used to better interpret the current image, diagnose the patient, choose a treatment approach, and schedule follow-up appointments. Notably, the synthesized image 304 displayed on the GUI 300 can, in some examples, be utilized to generate the final output of one or more additional interfaces, such as those described next.

Figure 4:
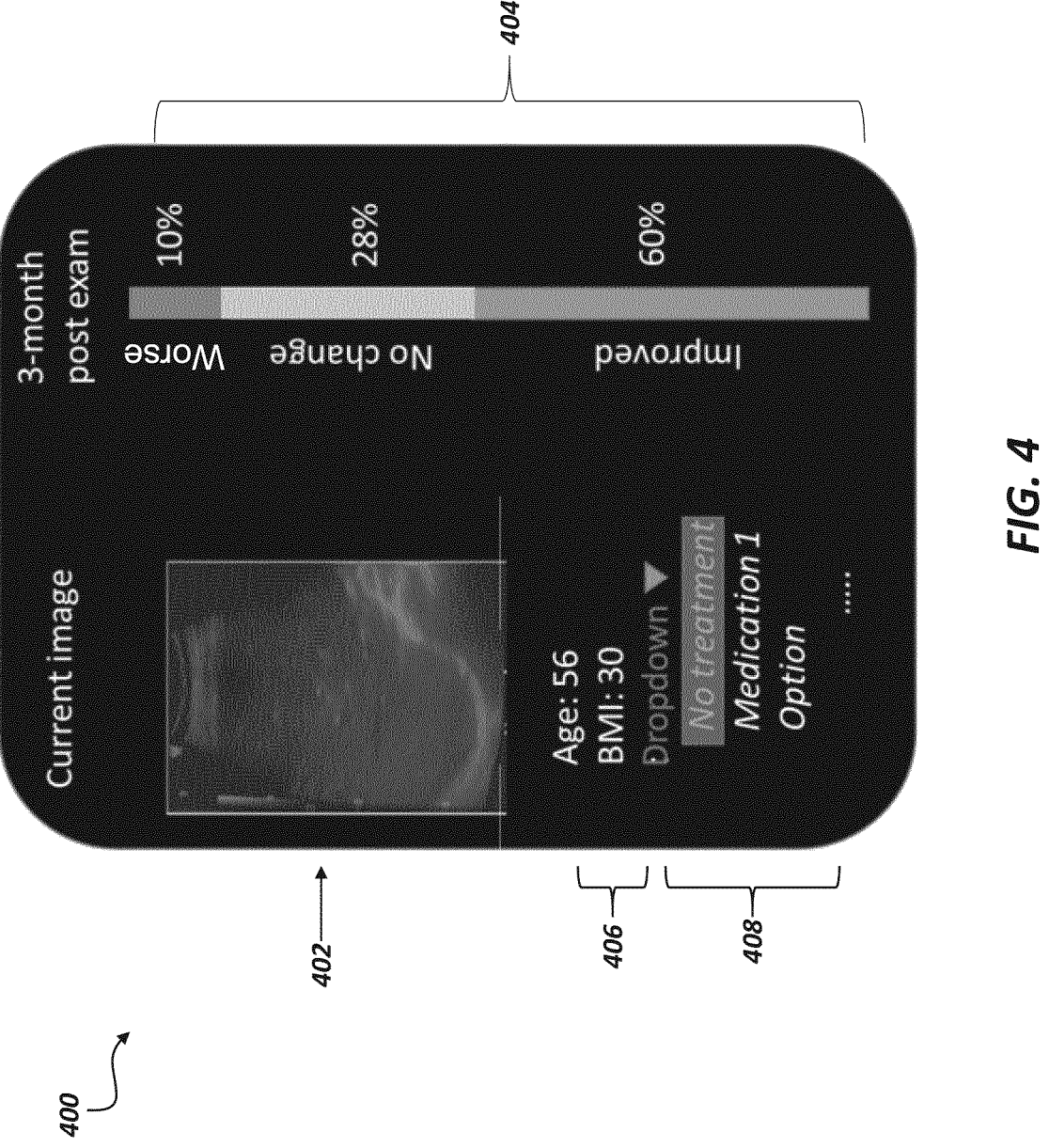
FIG. 4 is a graphical user interface configured to generate and display probabilities of various clinical outcomes based on a current image in accordance with embodiments of the present disclosure.

FIG. 4 shows a GUI 400 configured to generate future outcome probabilities based on a current image, at least one patient characteristic, and a selected treatment approach. In the illustrated example, the current image 402 is shown adjacent to an outcome probability chart 404. Like the GUI shown in FIG. 3, GUI 400 can also be configured to display patient-specific information 406 and a plurality of selectable treatment options, also represented in this example as a treatment dropdown menu 408. The GUI can provide various potential outcomes and the probabilities that such outcomes may occur at some future point, again selectable by a user. As mentioned above in connection with system 200, such outcomes may include a "worse" outcome, a "no change" outcome, and an "improved" outcome in some embodiments. Given the patient information received at and/or obtained by the GUI 400, e.g., age 56 and BMI 30, and as a result of not implementing any treatments, the GUI 400 shown indicates that there is a 60% chance that the disease feature captured in the current image 402 will be improved after about three months, and a 28% chance that the disease feature will not change after three months. There is also a 10% chance that the disease feature will become worse after three months.

Figure 5:
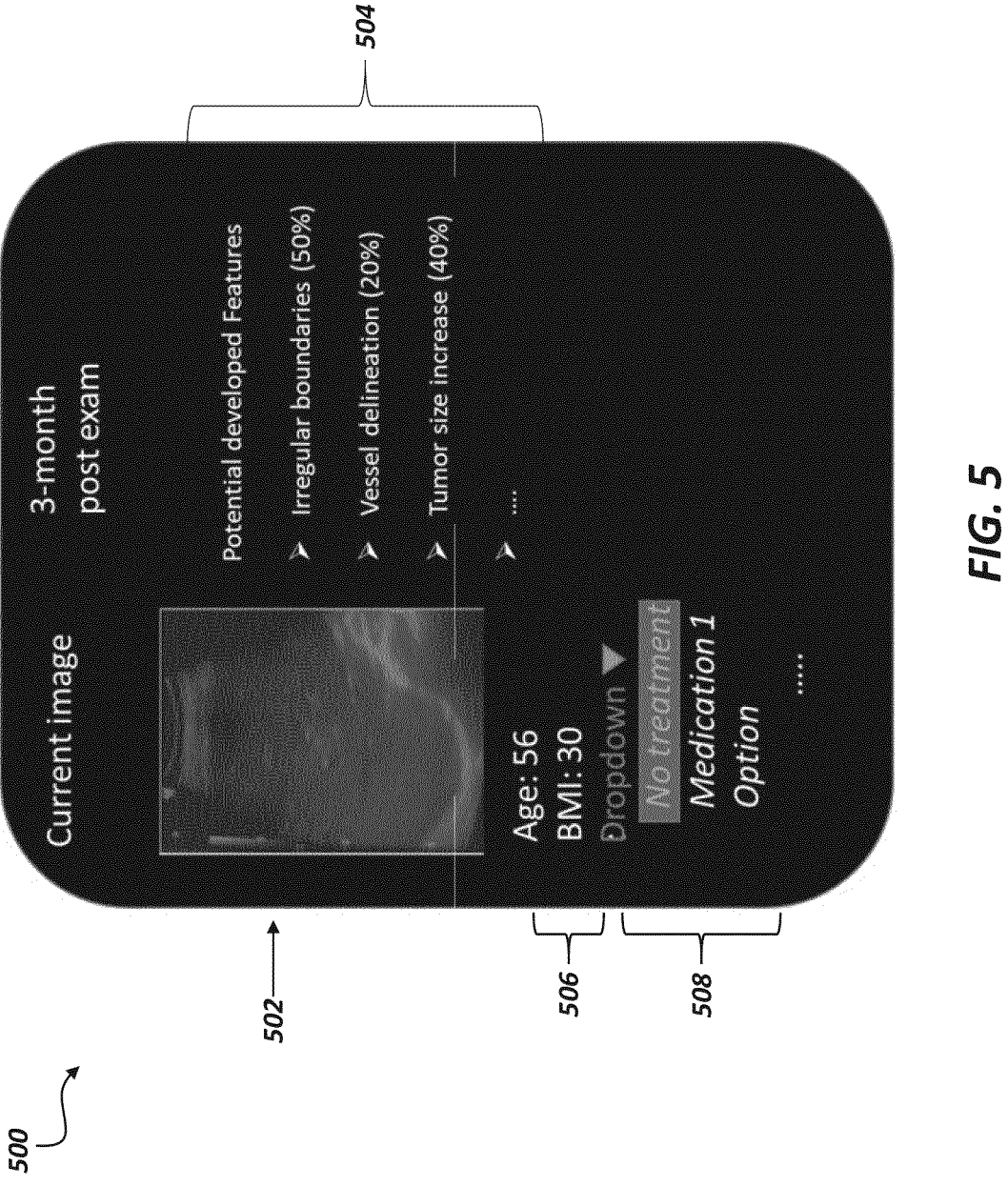
FIG. 5 is a graphical user interface configured to generate and display a list of potential future outcomes in accordance with principles of the present disclosure.

FIG. 5 shows a GUI 500 configured to generate a list of potential future outcomes in the form of feature descriptors or captions based on a current image. The GUI 500 shown includes a current image 502 and an outcome descriptor list 504. The GUI 500 also displays a list of patient-specific factors 506, here including the patient's age and BMI, along with a treatment dropdown menu 508. This user interface may provide a user with key features that may not be obvious in the current image but may develop in accordance with the disease progression learned through the neural network training process. Selecting this option may have the added benefit of directing the user's focus by drawing his/her attention to specific features when examining the current image 502, which may further decrease the likelihood of a missed diagnosis. The specific features detected within the image or predicted to develop over time may also inform the treatment approach selected by the user. For example, the system may determine that angiogenesis is likely to occur soon, which may cause the user to prescribe a medication or treatment approach tailored specifically to reducing or preventing angiogenesis.

As shown for illustrative purposes, the imaged patient is again 56 years old and has a BMI of 30. In response to selecting the "no treatment" plan from the dropdown menu 508, the outcome descriptor list 504 shows that there is a 50% chance that irregular boundaries will develop around the diseased feature after three months, a 20% chance that vessel delineation will begin or continue, and a 40% chance that the tumor recognized in the current image 502 will increase in size. The user can select a different treatment approach, thereby prompting the system to generate new estimated outcomes. For example, if the user selects Medication 1 from the treatment dropdown menu 508, the likelihood that the detected tumor will increase in size may decrease to about 10%, for example. Alternatively, the selection of Medication 1 may not change the estimations of disease feature development, such that the likelihood of continued tumor growth may remain at 40%. This scenario may prompt the user to refrain from prescribing Medication 1, especially if the other estimations remain the same as well. The potential outcomes displayed on the GUI 500 may change depending on the specific disease features detected by the underlying extraction network. For example, for a patient showing liver inflammation in the current image, and based on the patient's age group and BMI, the future outcome list 504 may indicate that there is a 40% probability that the liver inflammation will go away in 1 month with a treatment consisting solely of a change in the patient's diet.

The ground truth used to train the neural networks communicating with GUI 500 can be provided by expert labeling of the features extracted by the neural network over time. In this manner, the systems disclosed herein may not be limited to a set of pre-defined categories and may instead be allowed to expand as new information is gathered via repeated image acquisition.

In additional embodiments, one or more of the systems disclosed herein may be configured to predict the time period after which a potential change is likely to become obvious, diagnosable or dangerous. This information can then be used to schedule a follow-up examination earlier or later than when the standard schedule would otherwise dictate.

Figure 6:
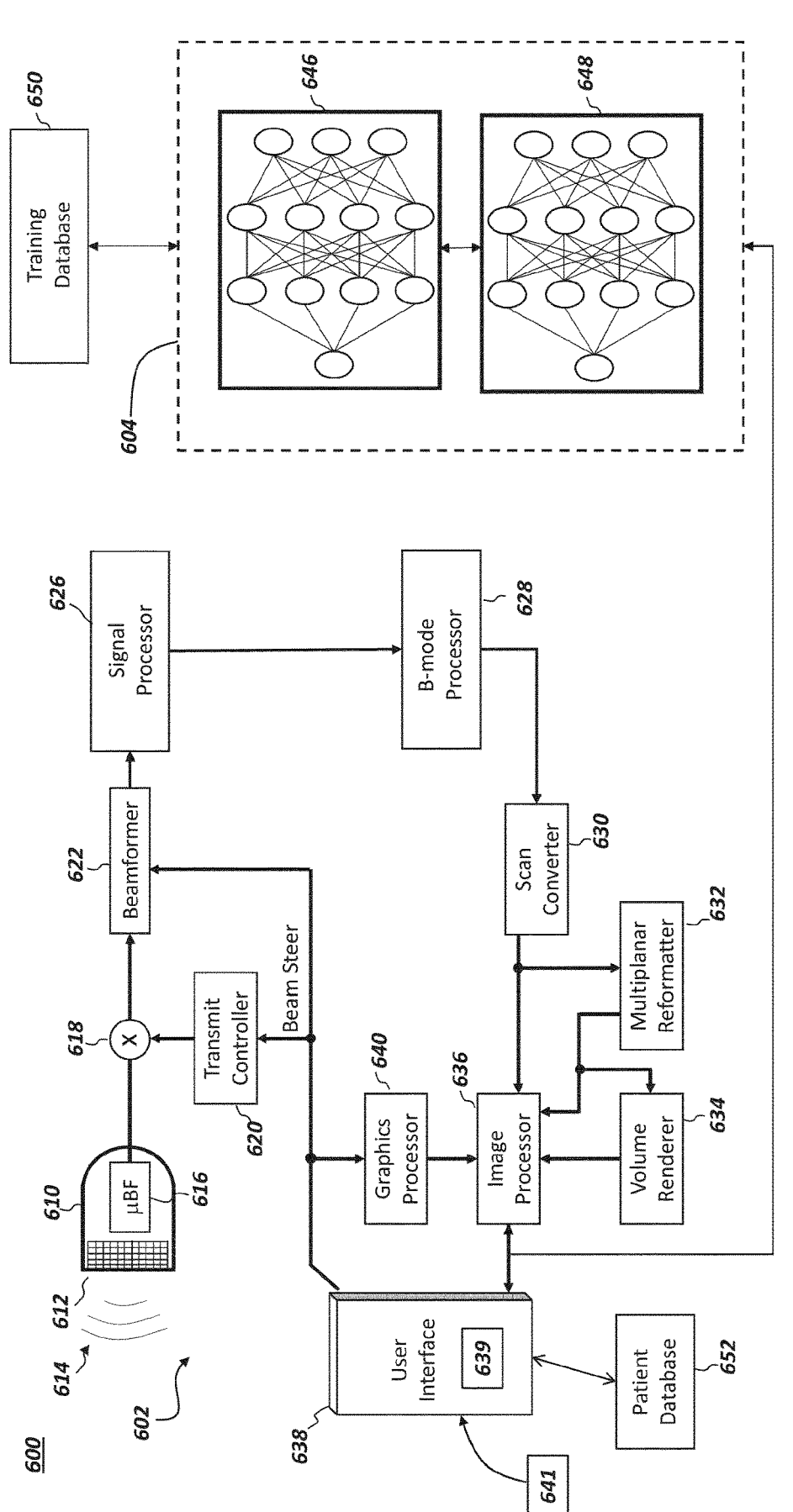
FIG. 6 is a block diagram of an operational arrangement of system components implemented in accordance with principles of the present disclosure.

The embodiments described herein are not limited to one particular form of image acquisition. FIG. 6 shows one example of an ultrasound-based disease prediction system 600 that may be implemented. As shown, the system 600 can include an ultrasound acquisition system 602 and one or more processors constituting a neural network system 604 communicatively, functionally, or physically coupled thereto.

The ultrasound acquisition system 602 may include an ultrasound probe 610 featuring a transducer array 612 for transmitting ultrasonic waves 614 into a target region and receiving echo information responsive to the transmitted waves. The target region may include a portion of a patient body containing, or suspected to contain, a disease feature. In various embodiments, the transducer array 612 may be a matrix array or a one-dimensional linear array. The transducer array 612 may be coupled to a microbeamformer 616 in the probe 610 which may control the transmission and reception of signals by the transducer elements in the array. In the example shown, the microbeamformer 616 is coupled by the probe cable to a transmit/receive (T/R) switch 618, which switches between transmission and reception and protects the main beamformer 622 from high energy transmit signals. In some embodiments, the T/R switch 618 and other elements in the system can be included in the transducer probe rather than in a separate ultrasound system component. The transmission of ultrasonic beams from the transducer array 612 under control of the microbeamformer 616 may be directed by the transmit controller 620 coupled to the T/R switch 618 and the beamformer 622, which receives input, e.g., from the user's operation of a user interface 638, which may display or be coupled with a control panel 639. A function that may be controlled by the transmit controller 620 is the direction in which beams are steered. The partially beamformed signals produced by the microbeamformer 616 are coupled to a main beamformer 622 where partially beamformed signals from individual patches of transducer elements are combined into a fully beamformed signal.

The beamformed signals may be communicated to a signal processor 626. The signal processor 626 may process the received echo signals in various ways, such as bandpass filtering, decimation, I and Q component separation, and/or harmonic signal separation. The signal processor 626 may also perform additional signal enhancement via speckle reduction, signal compounding, and/or noise elimination. In some examples, data generated by the different processing techniques employed by the signal processor 626 may be used by a data processor and/or at least one neural network to identify one or more disease features.

The processed signals may be coupled to a B-mode processor 628, which may employ amplitude detection for imaging structures in the body. The signals produced by the B-mode processor 628 may be coupled to a scan converter 630 and a multiplanar reformatter 632. The scan converter 630 may arrange the echo signals in the spatial relationship from which they were received in a desired image format. For instance, the scan converter 630 may arrange the echo signals into a two dimensional (2D) sector-shaped format. The multiplanar reformatter 632 may convert echoes which are received from points in a common plane in a volumetric region of the body into an ultrasonic image of that plane, as described in U.S. Pat. No. 6,443,896 (Detmer). In some examples, a volume renderer 634 may convert the echo signals of a 3D data set into a projected 3D image as viewed from a given reference point, e.g., as described in U.S. Pat. No. 6,530,885 (Entrekin et al.).

The 2D or 3D images may be communicated from the scan converter 630, multiplanar reformatter 632, and volume renderer 634 to an image processor 636 for further enhancement, buffering and/or temporary storage for display on the user interface 638, which can be configured to receive one or more user inputs 641. The user inputs 641 can comprise instructions for obtaining specific outputs, such as a synthesized future image or an outcome probability chart. The user inputs 641 can also include information about a patient, e.g., age or BMI. The user inputs 641 can also include one or more treatment options or desired time points. In some examples, a patient database 652 may also be communicatively coupled with the user interface 638. The patient database 652 may store information about a patient or a plurality of patients. The patient database 652 may be controlled by a hospital in some embodiments. Upon providing the proper authentication information, a user of the system 600 may be granted access to the patient database 652, allowing the user to retrieve details specific to a patient, including the patient's age, weight, BMI, etc. This information can be displayed on the user interface 638 and incorporated into the input received by the processor(s) of the neural network system 604.

A graphics processor 640 can generate graphic overlays for display with the ultrasound images. These graphic overlays may contain, e.g., standard identifying information such as patient information, date and time of the image, imaging parameters, and image feature labels, along with selectable treatment options and time points. Output generated from one or more neural networks can also be displayed.

The neural network system 604, which may comprise one or more computer processors, circuits or modules, can be communicatively coupled with various components of the ultrasound acquisition system 602. In the embodiment shown, the neural network system 604 is coupled with the user interface 638 and/or image processor 636.

Output generated by the first neural network 646, e.g., feature extraction network, can be input into one or more second neural networks 648, e.g., policy networks, which are configured to generate a one or more predictions of disease progression in the form of synthesized future images, outcome probabilities, and/or disease feature descriptors/captions. In some examples, a user input 641 received at the user interface 638 can include a selection of one or more of the second neural networks 648. The neural network system 604 can also be coupled to a training database 650, which may be integral to or separate from the overall system 600. The training database 650 may provide a large sample of images used to train the neural networks, for example including longitudinal samples of images taken at different stages of various diseases. Communication between the training database 650 and the neural network system 604 can be bidirectional, such that the training database 650 may provide images to the neural networks 646, 648 for training purposes, and the neural networks 646, 648 can transmit images for storage in the training database 650, thereby increasing the image sample size and further refining future output from the neural networks.

FIG. 7 is a flow diagram of a method of predicting and/or modeling disease progression performed in accordance with embodiments of the present disclosure. The example method 700 shows the steps that may be utilized, in any sequence, by the systems and/or apparatuses described herein for extracting disease features from an image and predicting the future progression of a medical condition associated with such features. Although examples of the present system have been illustrated with particular reference to ultrasound imaging modalities, the present system can be extended to other medical imaging systems where one or more images are obtained in a systematic manner. For example, the method 700 may be performed with the aid of one or more imaging systems including but not limited to MRI or CT.

In the embodiment shown, the method 700 begins at block 702 by "generating at least one image of a target region within a patient." At block 704, the method involves "applying a first neural network to the image, the first neural network configured to extract a disease feature from the image to produce a disease feature output." At block 706, the method involves "selecting a second neural network, different from the first neural network, from a plurality of neural networks." At block 708, the method involves "inputting the disease feature output to the second neural network in response to a user input." At block 710, the method involves "applying the second neural network to the disease feature, the second neural network configured to generate a predicted outcome of the disease feature at a future time point." At block 712, the method involves "displaying the predicted outcome generated by the second neural network."

In various examples, a neural network disclosed herein may be trained to synthesize a projected image of a disease feature based on a current image and user input instructing the system to generate the projected image at a specified future point in time. In addition or alternatively, a neural network may be trained to generate probabilities of various clinical outcomes based on a current image and user input. A neural network may also be trained to generate the likelihood and/or magnitude of specific disease progression indicators, such as increases in tumor size. Each of the neural networks may be configured to generate a different output based on patient-specific factors and/or potential treatment options available to a clinician. In this manner, systems disclosed herein may be configured to not only identify potentially harmful disease features within the body, e.g., tumors or lesions, but to predict how such features may develop over time without, or in response to, an assortment of treatments.

In various embodiments where components, systems and/ or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the disclosure. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Accordingly, the present system may be used to obtain and/or project image information related to, but not limited to renal, testicular, breast, ovarian, uterine, thyroid, hepatic, lung, musculoskeletal, splenic, and cardiac applications. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A disease prediction system comprising:
one or more processors in communication with an image acquisition device and configured to:
transform, with a first neural network, at least one image of a target region within a patient, to extract a disease feature from the image that was input to the first neural network to produce a disease feature output;
input the disease feature output to a second neural network, different from the first neural network, in response to a user input; and
transform, with the second neural network, the disease feature output, where the second neural network is configured to output a predicted outcome indication of the disease feature at a future time point,
wherein the second neural network is selected from a plurality of policy neural networks comprising a first policy neural network configured to generate a synthesized image of the disease feature and a second policy neural network configured to generate a list of disease descriptors.

2. The disease prediction system of claim 1, wherein the user input comprises a selection of the synthesized image of the diseased feature, or the list of future disease features.

3. The disease prediction system of claim 1, wherein the user input comprises a treatment option, patient-specific information, or both.

4. The disease prediction system of claim 1, wherein the disease feature comprises a tumor, a lesion, an abnormal vascularization, or a combination thereof.

5. The disease prediction system of claim 1, further comprising:
a graphical user interface configured to receive the user input and display the predicted outcome indication of the disease feature at the future time point,
wherein the image acquisition device is configured to generate the at least one image of the target region within the patient, and wherein the image acquisition system comprises an ultrasound system, an MRI system, or a CT system.

6. The disease prediction system of claim 1, wherein the future time point is selectable by a user and is between one week and one year from a current date.

7. The disease prediction system of claim 1, wherein the first neural network is operatively associated with a training algorithm configured to receive an array of training inputs and known outputs, wherein the training inputs comprise a longitudinal sample of images obtained from patients having a medical condition, and the known outputs comprise images of the disease feature.

8. The disease prediction system of claim 1, wherein the second neural network is operatively associated with a training algorithm configured to receive a second array of training inputs and known outputs, wherein the training inputs comprise the disease feature and the known outputs comprise the predicted outcome.

9. A method of disease prediction, the method comprising:
generating at least one image of a target region within a patient;
applying a first neural network to the image, the first neural network configured to extract a disease feature from the image to produce a disease feature output;
inputting the disease feature output to a second neural network, different from the first neural network, in response to a user input;
applying the second neural network to the disease feature, the second neural network configured to generate a predicted outcome of the disease feature at a future time point; and
displaying the predicted outcome generated by the second neural network, wherein the second neural network is selected from a plurality of policy neural networks comprising a first policy neural network configured to generate a synthesized image of the disease feature and a second policy neural network configured to generate a list of disease descriptors.

10. The method of claim 9, wherein the user input comprises a selection of the synthesized image of the diseased feature, or the list disease descriptors.

11. The method of claim 9, wherein the user input comprises a treatment option, patient-specific information, or both.

12. The method of claim 9, wherein the disease feature comprises a tumor, a lesion, an abnormal vascularization, or a combination thereof.

13. The method of claim 9, wherein generating the at least one image of the target region within the patient comprises acquiring ultrasound echoes generated in response to ultrasound pulses transmitted at the target region.

14. A non-transitory computer-readable medium comprising executable instructions, which when executed, cause a processor of a disease progression prediction system to:

apply a first neural network to at least one image of a target region within a patient, the first neural network configured to extract a disease feature from an image to produce a disease feature output;

input the disease feature output to a second neural network, different from the first neural network, in response to a user input; and apply the second neural network to the disease feature, the second neural network configured to generate a predicted outcome of the disease feature at a future time point, wherein the second neural network is selected from a plurality of policy neural networks comprising a first policy neural network configured to generate a synthesized image of the disease feature er and a second policy neural network configured to generate a list of disease descriptors.

* * * * *